United States Patent [19]

Orsolini et al.

[11] Patent Number: 5,192,741

[45] Date of Patent: Mar. 9, 1993

[54] SUSTAINED AND CONTROLLED RELEASE OF WATER INSOLUBLE POLYPEPTIDES

[75] Inventors: Piero Orsolini, Martigny; Rolland-Yves Mauvernay; Romano Deghenghi, both of Lausanne, all of Switzerland

[73] Assignee: Debiopharm S.A., Lausanne, Switzerland

[21] Appl. No.: 247,060

[22] Filed: Sep. 20, 1988

[30] Foreign Application Priority Data

Sep. 21, 1987 [GB] United Kingdom ............... 8722134

[51] Int. Cl.$^5$ ..................... A61K 37/26; C07K 7/40
[52] U.S. Cl. ............................ 514/4; 514/3; 514/12; 514/13; 514/14; 514/15; 514/16; 530/303; 530/304
[58] Field of Search ............. 514/12, 13, 14, 15, 514/16, 3, 4, 16; 530/303, 304

[56] References Cited

U.S. PATENT DOCUMENTS

| | | | |
|---|---|---|---|
| 4,010,125 | 3/1977 | Schally et al. | 260/8 |
| 4,622,244 | 11/1986 | Lapka et al. | 427/213.32 |
| 4,675,189 | 6/1987 | Kent et al. | 424/490 |
| 4,767,628 | 8/1988 | Hutchison | 424/426 |

FOREIGN PATENT DOCUMENTS

| | | |
|---|---|---|
| 52510 | 6/1982 | European Pat. Off. . |
| 58481 | 8/1982 | European Pat. Off. . |
| 204476 | 12/1986 | European Pat. Off. . |
| 0211267 | 2/1987 | European Pat. Off. . |
| 251476 | 1/1988 | European Pat. Off. . |
| 302582 | 2/1989 | European Pat. Off. . |

OTHER PUBLICATIONS

Chang, "Biodegradable Semipermeable Microcapsules Containing Enzymes, Hormones, Vaccines and Other Biologicals", J. Bioeng., 1, (1976), p. 25.

Langer, "Controlled Release of Macromolecules", Chemtech., Feb. 1982, pp. 98–105.

Hutchison et al., "Biodegradable Carriers for the Sustained Release of Polypetides", TIBTECH, Apr. 1987, (vol. 5), pp. 102–106.

Chemical Abstracts, vol. 107, No. 13, abstract 109765g (1987).

*Primary Examiner*—Ronald W. Griffin
*Attorney, Agent, or Firm*—Pennie & Edmonds

[57] ABSTRACT

There is disclosed a pharaceutical composition for sustained and controlled release of drug over an extended period of time comprising a polylactide, a copolymer of lactic and glycolic acid, a mixture of such polymers and a water-insoluble peptide which, when placed in an aqueous physiologically-type environment releases the peptide in continuous manner for a period of at least one week, and with an initial release for the first twenty-four hours of not more than 30% of the total amount released. There is thus provided the control of the release pattern and in general a decrease of the initial burst effect.

14 Claims, No Drawings

SUSTAINED AND CONTROLLED RELEASE OF WATER INSOLUBLE POLYPEPTIDES

DESCRIPTION

This invention relates to pharmaceutical compositions of therapeutically active but water-insoluble polypeptides, which provide a continuous, controlled and sustained release of such peptides when placed in a physiological-type environment by means of implant or injections under the skin or into the muscle of animals and humans.

This invention is further characterized by the use of bio-degradable and bio-compatible polymers and co-polymers as matrix in which the water-insoluble polypeptides are dispersed or encapsulated.

The need of producing sustained release of peptides for parenteral administration has been recognized for a long time (cf. T. M. S. Chang "Biodegradable Semipermeable Microcapsules containing enzymes, hormones, vaccines and other biologicals" in J. Bioengineering 1, 25 (1976); R. Langer "Controlled Release of Macromolecules" in Chemtech, February 1982, pp 98-105; F. G. Hutchinson and B. J. A. Furr "Biodegradable carriers for the sustained release of polypeptides" in TIBTECH, April 1987 (vol. 5) pp 102-106.

A number of such formulations, but applied to water soluble polypeptides, have been described in EPS 0052510 "Microencapsulation of water soluble polypeptides", published Aug. 27, 1986 and in EPS 0058481 "Continuous release pharmaceutical compositions", published Oct. 1, 1986.

The novel, surprising and totally unexpected feature of the present invention resides in the fact that therapeutically useful sustained and controlled release compositions can advantageously be obtained by using essentially water-insoluble peptides, possessing immeasurably low solubility in aqueous solution at room or body temperature and yet providing an effective and controlled release of such peptides when their compositions are administered parenterally in a physiologic, essentially aqueous environment.

It is a novel and surprising consequence of the present invention that polypeptides which are normally water soluble in nature or when prepared by synthesis, can be advantageously rendered water insoluble by forming insoluble addition salts, such as with pamoic acid, tannic acid, stearic acid and other non-toxic water-insoluble acids, prior to their microencapsulation or dispersion in a biodegradable polymeric matrix.

The use of sparingly soluble or water insoluble derivatives is of course well known, even in the peptide field (cf Schally et al. U.S. Pat. No. 4,010,125 Mar. 1, 1977, column 7, line 25), when slow-release depot dosage forms are needed.

However, when biodegradable polymers such as polylactic acid polyglycolic acid, polyhydroxybutyric acid, polyortho-esters, polyacetals and the like are used as drug delivery systems, the release of the peptides in a continuous manner has consistently required an appreciable water solubility. Reported experiments have shown that the biodegradation of polymers (such as polylactide and polylactide-co-glycolide for example) leads to water-uptake and generation of aqueous channels or pores from which peptides leak out because they are water soluble.

Our discovery that peptides can be released from matrixes and microcapsules with a highly desirable release pattern when their water solubility is diminished down to practically zero levels is totally surprising and contradicts the teachings of the prior art. In particular we found that the release of certain peptides, such as D-Trp$^6$-LHRH, from polymeric matrixes, is better in terms of uniformity and duration, the more water-insoluble the addition salt of the peptide is.

"Water-insolubililty" is hereby defined as the amount of peptide which can be measured in solution when the salt is dispersed or stirred for 4 hours in distilled water at temperatures of 40° C. or below, such amount being 25 mg/l or less (0 to 25 ppm).

It is highly desirable to administer biologically active polypeptides continuously and for a sustained period of time, from one week to several months. It is also highly desirable that the pattern of release be controlled, so as to avoid uneven releases of the peptide at the beginning, in the middle or at the end of the therapeutic cycle. It has been often found that peptides are released from biodegradable matrixes in bursts (also called burst effects), either at the beginning of the cycle or at the end, when the polymeric matrix is eroded through hydrolysis.

An important feature of the present invention is a control of the release pattern, and in general a decrease of the initial burst effect. The water insoluble peptide is released to a lesser extent that its water soluble derivatives, thus affording a more prolonged release time and the avoidance of over-dosing the patient. By transforming a normally water soluble peptide into an insoluble one, we are able to limit the initial burst effect (i.e. the amount of peptide released in the first 24 hours) to less than 30% of the total dose.

EXAMPLE I

Fifty grams of a copolymer of D,L-lactide and glycolide with a 50/50 molar ratio of D,L-lactide to glycolide and an average molecular weight of 50,000 is dissolved in 950 grams of methylene chloride.

The solution is passed through a millipore filter to remove any particulate matter and pyrogens. To this solution, one gram of D-Trp$^6$ LHRH pamoate is added and dispersed with a high shear mixer.

The resulting mixture is placed in a rotating evaporator and the majority of the methylene chloride is removed under vacuum. The resulting thick dispersion is poured onto a glass plate and spread with an adjustable blade set at 0.7 mm.

After air drying the resulting film is vacuum desiccated for 48 hours and then extruded through a 0.8 mm orifice at 70° C. under pressure. The resulting rods are ground cryogenically at −40° C.

The resulting granular material is sieved through a 180 micrometer screen and the undersize fraction is collected and sterilized by exposure to gamma radiation between 2.5 and 2.8 Mrad.

EXAMPLE II

The same procedure as in example I is followed by substituting D-Trp$^6$-LHRH pamoate with D-Trp$^6$-LHRH stearate salt.

EXAMPLE III

The same procedure as in example I is followed with the pamoate salt of

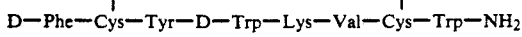

as the water insoluble peptide.

EXAMPLE IV

The procedure of example I is applied to one of following water-insoluble pamoate salts:
D-Nal(2)[6] LHRH pamoate
D-Ser(0-tBu)[6]-des Gly[10]-Azgly[10]-LHRH pamoate
D-Ser(But)[6] LHRH(1-9) ethylamide pamoate
D-Leu[6]-des Gly[10]-LHRH ethylamide pamoate

EXAMPLE V

The procedure of examples I to IV is followed with D,L lactide-co-glycolide polymers in which the molar ratio was 67% D,L lactide 33% glycolide, 75% D,L lactide 25% glycolide or 100% D,L lactide.

EXAMPLE VI

The procedure of examples I to V is followed with the water-insoluble pamoate, tannate or stearate salts of one of the following peptides: oxytocin, vasopressin, ACTH, calcitonin, epidermal growth factor, prolactin, inhibin, interferon, LHRH, somatostatin, insulin, glucagon, atrial natriuretic factor, endorphin, a renin inhibitor, GHRH, peptide-T, or synthetic analogues and modifications thereof.

Release Pattern in Animals (rats)

A typical release pattern of an implanted formulation of D-Trp[6]-LHRH pamoate in rats is the following: ng/ml of radio-assayed D-Trp[6]-LHRH in plasma (mean of six rats): (t₀) 0.04, (1 hr) 7.74, (6 hrs) 0.80, (day 2) 0.85, (day 4) 0.77, (day 7) 0.25, (day 11) 0.12, (day 14) 0.11, (day 18) 0.11, (day 21) 0.14, (day 25) 0.18.

In an alternate embodiment of the invention, the composition is prepared by dispersing a water-insoluble peptide salt into a solution of a polyactide polymer, a polyglycolide polymer, a copolymer of lactic and glycolic acids or a mixture of such polymers and adding a coacervation agent to form a plurality of microcapsules. The resulting microcapsules, which may range in size from 1 to 500 μm, are poured into a pharmaceutically acceptable hardening liquid and then collected for use as the pharmaceutical composition.

The preceding examples are not limitative to the described water-insoluble peptides or to the biodegradable polymers used, as it is apparent to a person skilled-in-the-art.

We claim:

1. A process for preparing a pharmaceutical composition designed for sustained and controlled release of a peptide, said process comprising selecting a water-insoluble peptide salt; dispersing the water-insoluble peptide salt into a solution of a polylactide polymer, a polyglycolide polymer, a copolymer of lactic and glycolic acids, or a mixture of said polymers and a solvent; removing the solvent of the solution to form a residue; and shaping the residue into solid particles of said pharmaceutical composition suitable for administration by parenteral injection or as a subcutaneous implant.

2. A process for preparing a pharmaceutical composition designed for sustained and controlled release of a peptide, said process comprising selecting a water insoluble peptide salt; dispersing a water-insoluble peptide salt into a solution of a polylactide polymer, a polyglycolide polymer, a copolymer of lactic and glycolic acids or a mixture of said polymers; adding a coacervation agent to the solution to form microcapsules of the peptide salt and polymer(s); pouring the resulting microcapsules into a pharmaceutically acceptable hardening liquid; and collecting the microcapsules for use as a pharmaceutical composition suitable for administration by parenteral injection or as a subcutaneous implant.

3. A process as claimed in claim 1 or 2 which further comprises selecting said water-insoluble peptide from pharmaceutically acceptable salts of LHRH and synthetically prepared analogues thereof.

4. A process as claimed in claim 3 wherein the pharmaceutically acceptable salt is selected from the group consisting of pamoate, tannate and stearate salts.

5. A process as claimed in claim 1 or 2 which further comprises selecting said water-insoluble peptide from pharmaceutically acceptable salts of oxytocin, vasopressin, ACTH, calcitonin, epidermal growth factor, prolactin, inhibin, interferon, somatostatin insulin, glucagon, atrial natriuretic factor, endorphin, a peptide renin inhibitor, growth hormone releasing factor, peptide T and synthetic analogues thereof.

6. A process as claimed in claim 1 or 2 wherein said water-insoluble peptide salt is dispersed within said solution by high shear mixing.

7. A process as claimed in claim 1 or 2 which further comprises sterlizing said composition by exposure to gamma radiation at between 2.5 and 2.8 Mrad.

8. The process of claim 1 wherein said peptide, polymer or copolymer is selected so as to provide a continuous release of said peptide when placed in a physiological environment.

9. The process of claim 1 further comprising selecting a water-insoluble peptide and polylactide polyglycolide polymer or copolymer molar ratio, and dosing said polymer or copolymer with said peptide salt so that said subcutaneous implant provides a continuous release of peptide when placed in a physiological environment.

10. The process of claim 2 further comprising selecting a water-insoluble peptide and polylactide polyglycolide polymer or copolymer molar ratio, and dosing said polymer or copolymer with said peptide salt so that said microspheres provide a continuous release of peptide when placed in a physiological environment.

11. A process for preparing a pharmaceutical composition for sustained and controlled release of a peptide, said process comprising:
forming a water-insoluble salt of LHRH or a synthetic analog thereof;
dispersing the water-insoluble peptide salt with mixing into a solution of a polylactide polymer, a polyglycolide polymer, a copolymer of lactic and glycolic acids or a mixture of said polymers and a solvent;
forming microparticles of the peptide salt and polymer(s) by evaporating the solvent;
drying the microparticles;
extruding the microparticles into rods;
grinding the rods into granular material;
sieving the granular materials; and
collecting a fraction and sterlizing the fraction for use as the pharmaceutical composition.

12. A process for preparing a pharmaceutical composition designed for sustained and controlled release of a peptide, said process comprising forming a water insoluble peptide salt from a water-soluble peptide; dispersing said water-insoluble peptide salt into a solution of a polylactide polymer, a polyglycolide polymer, a copolymer of lactic and glycolic acids or a mixture of said polymers; adding a coacervation agent to the solution to form microcapsules of the peptide salt and polymer(s); pouring the resulting microcapsules into a pharmaceutically acceptable hardening liquid; and collecting the microcapsules for use as a pharmaceutical composition suitable for administration by parenteral injection or as a subcutaneous implant.

13. The process of claim 12, further comprising selecting said peptide from the group consisting of pamoate, tannate and stearate salts of D-Trp$^6$-LHRH and selecting a mixture of D,L-lactide and glycolide as said polymer.

14. The process of claim 11 wherein the rods are ground cryogenically into the granular material.

* * * * *